US009421509B2

(12) United States Patent
Arai

(10) Patent No.: US 9,421,509 B2
(45) Date of Patent: Aug. 23, 2016

(54) HYDROCARBON PRODUCTION APPARATUS AND HYDROCARBON PRODUCTION PROCESS

(75) Inventor: Shinya Arai, Tokyo (JP)

(73) Assignees: Japan Oil, Gas and Metals National Corporation, Tokyo (JP); INPEX CORPORATION, Tokyo (JP); JX Nippon Oil & Energy Corporation, Tokyo (JP); Japan Petroleum Exploration Co., Ltd., Tokyo (JP); COSMO OIL CO., LTD., Tokyo (JP); NIPPON STEEL & SUMIKIN ENGINEERING CO., LTD., Tokyo (JP)

( * ) Notice: Subject to any disclaimer, the term of this patent is extended or adjusted under 35 U.S.C. 154(b) by 529 days.

(21) Appl. No.: 14/004,954

(22) PCT Filed: Mar. 13, 2012

(86) PCT No.: PCT/JP2012/056449
§ 371 (c)(1),
(2), (4) Date: Sep. 13, 2013

(87) PCT Pub. No.: WO2012/124701
PCT Pub. Date: Sep. 20, 2012

(65) Prior Publication Data
US 2015/0011662 A1 Jan. 8, 2015

(30) Foreign Application Priority Data
Mar. 17, 2011 (JP) ................................. 2011-059343

(51) Int. Cl.
*B01J 8/00* (2006.01)
*B01J 8/08* (2006.01)
Int'l Search Report issued May 22, 2012 in Int'l Application No. PCT/JP2012/056449.

(52) U.S. Cl.
CPC .. *B01J 8/08* (2013.01); *C07C 1/02* (2013.01); *C10G 2/00* (2013.01); *B01J 2208/00796* (2013.01); *C10G 2300/1022* (2013.01); *C10G 2300/304* (2013.01); *C10G 2300/4031* (2013.01)

(58) Field of Classification Search
CPC .............. B01J 8/00; B01J 8/08; B01J 19/00; B01J 19/24; B01J 2208/00796; C07C 1/00; C07C 1/02; C10G 2/00; C10G 2300/10; C10G 2300/1022; C10G 2300/20; C10G 2300/30; C10G 2300/304; C10G 2300/40; C10G 2300/4031
See application file for complete search history.

(56) References Cited

U.S. PATENT DOCUMENTS 6,822,006 B1  11/2004 O'Rear et al.
8,685,212 B2 * 4/2014 Tanaka ........................... 203/87
(Continued)

FOREIGN PATENT DOCUMENTS

EP      2199368 A1    6/2010
JP   2004-323626 A   11/2004
(Continued)

OTHER PUBLICATIONS

Extended European Search Report issued Jul. 23, 2014 in EP Application No. 12756963.0.
(Continued)

*Primary Examiner* — Natasha Young
(74) *Attorney, Agent, or Firm* — Panitch Schwarze Belisario & Nadel LLP

(57) ABSTRACT

The hydrocarbon production apparatus is provided with a gas-liquid separator for cooling gaseous state hydrocarbons drawn out from a gas phase portion of a reactor for the Fischer-Tropsch synthesis reaction and liquefying a portion of the hydrocarbons. A light liquid hydrocarbon supply line for supplying light hydrocarbons is disposed between a downstream side line which is downstream from the last stage of a gas-liquid separating unit of the gas-liquid separator, and an upstream side line which is upstream from the last stage of the gas-liquid separating unit of the gas-liquid separator, wherein the downstream side line is a liquid hydrocarbon line on the downstream side through which the light hydrocarbons having cloud points lower than the temperature at an outlet of a cooler in the last stage of the gas-liquid separating unit are flowed.

8 Claims, 3 Drawing Sheets

(51) Int. Cl.
 *B01J 19/00* (2006.01)
 *B01J 19/24* (2006.01)
 *C10G 2/00* (2006.01)
 *C07C 1/00* (2006.01)
 *C07C 1/02* (2006.01)

(56) References Cited

U.S. PATENT DOCUMENTS 9,120,981 B2 * 9/2015 Onishi .................... C10G 2/30

2010/0113625 A1 5/2010 Stickney et al.

FOREIGN PATENT DOCUMENTS

| JP | 2007-516065 A | 6/2007 |
| WO | 9915484 A1 | 4/1999 |
| WO | 2005005038 A1 | 1/2005 |
| WO | 2009027914 A2 | 3/2009 |
| WO | 2010038389 A1 | 4/2010 |
| WO | 2011024650 A1 | 3/2011 |
| WO | 2012023526 A1 | 2/2012 |

* cited by examiner

HYDROCARBON PRODUCTION APPARATUS AND HYDROCARBON PRODUCTION PROCESS

CROSS-REFERENCE TO RELATED APPLICATIONS

This application is a Section 371 of International Application No. PCT/JP2012/056449, filed Mar. 13, 2012, which was published in the Japanese language on Sep. 20, 2012, under International Publication No. WO 2012/124701 A1, and the disclosure of which is incorporated herein by reference.

TECHNICAL FIELD

The present invention relates to a hydrocarbon production apparatus and a hydrocarbon production process by using a slurry bubble column reactor according to the Fischer-Tropsch synthesis reaction.

Priority is claimed on Japanese Patent Application No. 2011-059343 filed on Mar. 17, 2011, the content of which is incorporated herein by reference.

BACKGROUND ART

In recent years, in view of reducing the environmental burden, there have been demanded environmentally friendly clean liquid fuels which are lower in sulfur content and aromatic hydrocarbon content. With the above view taken into account, as a technique capable of producing a fuel oil base stock which is free of sulfur and aromatic hydrocarbon content but rich in aliphatic hydrocarbon, in particular, kerosene and gas oil base stocks, there has been studied a process for utilizing the Fischer-Tropsch synthesis reaction (hereinafter, referred to as the "FT synthesis reaction") using carbon monoxide gas (CO) and hydrogen gas ($H_2$) as a feedstock gas. This method is that in which a natural gas is reformed to produce a synthesis gas (a mixed gas containing CO and $H_2$ as main components), the synthesis gas is subjected to the FT synthesis reaction, thereby synthesizing hydrocarbons with a wide carbon number distribution, and the obtained hydrocarbons are hydrogenated and fractionally distilled to produce liquid fuel base stocks. This is referred to as the GTL (Gas To Liquids) technique (refer to Patent Document 1, for example).

As a process for producing hydrocarbons by the FT synthesis reaction, there is also a known process using a slurry bubble column reactor in which a synthesis gas is blown into a slurry prepared by suspending solid catalyst particles within liquid hydrocarbons (hereinafter, from time to time simply referred to as "slurry") to conduct the FT synthesis reaction (refer to Patent Document 2, for example).

In the process using the slurry bubble column reactor, a gas phase portion at an upper part of the slurry inside the reactor is formed, and a line connected to an upper part of the reactor discharges through a synthesis gas which remains unreacted during passage through the slurry (unreacted synthesis gas) and light hydrocarbons which are produced by the FT synthesis reaction and kept in a gaseous state under conditions inside the reactor.

In the above-described slurry bubble column reactor, normally, in order to separate and recover the light hydrocarbons discharged through the line connected to the upper part of the reactor, the line is connected to a gas-liquid separator, gas components discharged from the upper part of the reactor are cooled by a cooler of the gas-liquid separator, and condensed light liquid hydrocarbons are separated from the gas components by a gas-liquid separation vessel. Then, the separated gas components containing an unreacted synthesis gas are recycled into the reactor, and separated liquid components (light liquid hydrocarbons) are supplied to a subsequent step of distillation together with heavy hydrocarbons to be described later. Here, the heavy hydrocarbons produced by the FT synthesis reaction are fundamentally drawn out as liquids from the slurry bed of the reactor, with a slight vapor pressure kept under conditions inside the reactor. Thus, the heavy hydrocarbons partially exist as a gas in a gas phase portion and discharged as a portion of the gas components discharged through the line. Further, liquid heavy hydrocarbons may be entrained with a gas in the form of droplets and contained in the discharged components.

CITATION LIST

Patent Document

Patent Document 1: Japanese Published Unexamined Patent Application No. 2004-323626

Patent Document 2: Japanese Translation of International Application No. 2007-516065

SUMMARY OF THE INVENTION

Technical Problem

Moreover, in the slurry bubble column reactor, where temporary stop of the FT synthesis reaction is required for some reason, for example, in a preliminary stage of start-up which starts to supply a synthesis gas (feedstock gas) from a state where operation is stopped, the supply of feedstock gas is stopped in some cases, nitrogen gas is recycled inside a reaction system, and operation is conducted so as to keep a slurry fluid although the reaction is stopped. Further, for example, in an intermediate stage to shift to normal operation from the above-described operation or the like, there is a case where regardless of a continuous supply of the feedstock gas, the reaction temperature is set to be lower than that during normal operation, by which the FT synthesis reaction is not substantially proceeded or operation is carried out at a reaction conversion ratio of carbon monoxide which is significantly lower than that during normal operation.

In the unsteady operation which has been described above, a cooler for cooling gas components discharged from the gas phase portion of the slurry bubble column reactor to cause partial liquefaction may undergo reduction in cooling efficiency, thus exhibiting a tendency toward temperature rise at an outlet of the cooler. This is due to the fact that heavy hydrocarbons which have been vaporized from slurry-constituting liquid hydrocarbons retained inside the slurry bubble column reactor into a portion of gaseous discharged components are cooled by the cooler, deposited, and adhered in a tube of the cooler in the form of a solid (wax). Thereby, continuous operation of an FT synthesis unit is rendered difficult due to the temperature rise at the outlet of the cooler. An extreme case may result in such a problem that the tube of the cooler is clogged.

Measures for coping with a trouble resulting from adhesion of wax fraction to the cooler as described above may include a method in which, for example, steam is used to melt and remove the adhered wax in a stage where the cooling efficiency of the cooler has been reduced to a certain level. However, in this case, temporary stop of operation of the gas-liquid separator is required to result in a reduced operation rate of the FT synthesis unit. Installing a plurality of gas-liquid separators in parallel so as not to stop operation of the gas-liquid separators has also been considered, however this would lead to an increase in the size and cost of facilities.

The present invention has been made in view of the above situation, an object of which is to provide a hydrocarbon production apparatus and a hydrocarbon production process in which in the production of hydrocarbons by using a slurry bubble column reactor according to the FT synthesis reaction, preventing a trouble resulting from adhesion of wax to a cooler of a gas-liquid separator in which gas components discharged from a gas phase portion of the reactor are cooled and partially liquefied to recover liquid components during unsteady operation.

Solution to Problem

The inventor of the present invention has found the following after diligent study in an attempt to achieve the above object.

The following reasons are assumed for the adhesion of wax inside the cooler. That is, as described above, heavy hydrocarbons contained in liquid hydrocarbons retained inside the slurry bubble column reactor are partially vaporized and entrained with gas components discharged from a gas phase portion of the reactor. During normal operation, in the gas-liquid separator, light hydrocarbons which are contained in the discharged gas components and discharged from the reactor are cooled in a large quantity by the cooler and condensed to produce light liquid hydrocarbons, and the light liquid hydrocarbons are flowed in a large quantity inside the cooler. Therefore, if the heavy hydrocarbons entrained with the gas components are cooled inside the cooler, it is considered to be "washed away" by a large quantity of the light liquid hydrocarbons without adhering inside the cooler. On the other hand, in a state that production of new hydrocarbons by the FT synthesis reaction is stopped or substantially suppressed, a large reduction in quantity of light hydrocarbons which are vaporized from the liquid hydrocarbons inside the reactor and discharged from the gas phase portion of the reactor as discharged gas components may be found. Thereby, the light liquid hydrocarbons condensed and produced in the cooler are substantially reduced in quantity, and at the same time an effect of "washing away" heavy hydrocarbons (wax) deposited in the form of a solid is considered to be substantially reduced.

Further, where operation is performed at a reaction temperature set to be lower than that during normal operation in order to substantially reduce a reaction conversion ratio of carbon monoxide, the adhesion of wax is assumed from characteristics of the FT synthesis reaction to be facilitated by an increase in the carbon number of hydrocarbons produced by the reaction, a relative decrease in the production quantity of light hydrocarbons and an increase in the production quantity of heavy hydrocarbons.

Then, on the basis of the above findings, the inventor has carried out a further study to accomplish the present invention.

That is, the hydrocarbon production apparatus of the present invention is a hydrocarbon production apparatus which retains internally slurry containing catalyst particles and liquid hydrocarbons to produce hydrocarbons by using a slurry bubble column reactor having a gas phase portion at an upper part of the slurry according to the Fischer-Tropsch synthesis reaction. The hydrocarbon production apparatus is provided with a gas-liquid separator having a plurality of gas-liquid separating units for cooling hydrocarbons which have been drawn out from the gas phase portion of the reactor and are in a gaseous state under conditions inside the reactor, thereby liquefying a portion of the hydrocarbons to conduct gas-liquid separation. Each of the plurality of gas-liquid separating units is provided with: a cooler; a gas-liquid separation vessel; a downstream side line which is downstream from the last stage of the gas-liquid separating unit of the gas-liquid separator, wherein a light liquid hydrocarbon line on the downstream side therein which light liquid hydrocarbons having cloud points lower than a temperature at an outlet of the cooler in the last stage of the gas-liquid separating unit are flowed therein; an upstream side line which is upstream from the last stage of the gas-liquid separating unit of the gas-liquid separator; and a light liquid hydrocarbon supply line which is disposed between the downstream side line and the upstream side line, and which supplies the light liquid hydrocarbons inside the light liquid hydrocarbon line on the downstream side to the upstream side line.

Further, in the hydrocarbon production apparatus, the light liquid hydrocarbon line on the downstream side may be a line which is connected to the last stage of the gas-liquid separating unit of the gas-liquid separator to discharge liquid hydrocarbons from the gas-liquid separating unit.

Still further, in the hydrocarbon production apparatus, the upstream side line may be a line positioned just before the last stage of the gas-liquid separating unit of the gas-liquid separator.

The hydrocarbon production process of the present invention is a hydrocarbon production process which retains internally slurry containing catalyst particles and liquid hydrocarbons to produce hydrocarbons by using a slurry bubble column reactor having a gas phase portion at an upper part of the slurry according to the Fischer-Tropsch synthesis reaction. The hydrocarbon production process is provided with a gas-liquid separation step in which a gas-liquid separator having a gas-liquid separating unit composed of a cooler and a gas-liquid separation vessel is used to cool hydrocarbons which have been drawn out from the gas phase portion of the reactor and are in a gaseous state under conditions inside the reactor, thereby performing gas-liquid separation after liquefaction of a portion of the hydrocarbons. While a reaction is stopped in the reactor or while a reaction conversion ratio of carbon monoxide is 20% or less in the reactor, the light liquid hydrocarbons having cloud points lower than a temperature at an outlet of the cooler in the last stage of the gas-liquid separating unit of the gas-liquid separator are supplied to an upstream side line which is upstream from the last stage of the gas-liquid separating unit of the gas-liquid separator.

Further, in the hydrocarbon production process, liquid hydrocarbons discharged from the last stage of the gas-liquid separating unit of the gas-liquid separator may be used as the light liquid hydrocarbons.

Still further, in the hydrocarbon production process, the light liquid hydrocarbons may be supplied to a line which is positioned just before the last stage of the gas-liquid separating unit of the gas-liquid separator.

Advantageous Effects of Invention

According to the hydrocarbon production apparatus of the present invention, it is possible to reliably prevent wax from adhering to the cooler in the last stage of the gas-liquid separating unit. Further, removal of the adhered wax makes it possible to prevent occurrence of a trouble resulting from the adhesion of wax without reduction in the operation rate of the FT synthesis unit or leading to an increase in size and cost of facilities.

Further, according to the hydrocarbon production process of the present invention, it is possible to prevent occurrence of a trouble resulting from the adhesion of wax without reduction in the operation rate of the FT synthesis unit or leading to an increase in the size and cost of facilities.

DESCRIPTION OF EMBODIMENTS

Hereinafter, a detailed description will be given about the hydrocarbon production apparatus and the hydrocarbon production process of the present invention.

First, a description will be given about the liquid fuel synthesizing system which includes one embodiment of the hydrocarbon production apparatus in the present invention with reference to FIG. 1.

Figure 1:
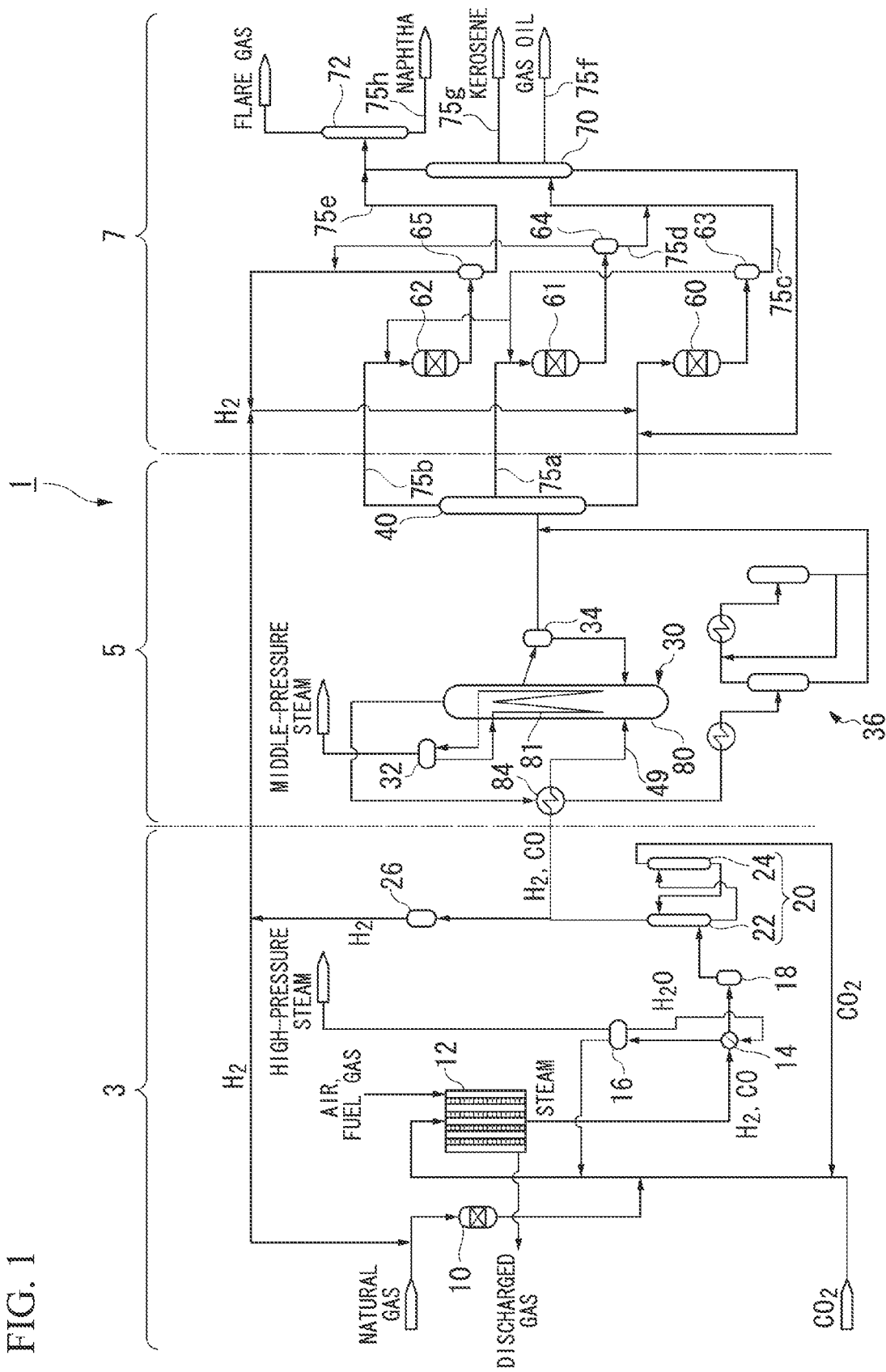
FIG. 1 is a schematic view which shows an entire constitution of one example of a liquid fuel synthesizing system of the present invention.

The liquid fuel synthesizing system 1 shown in FIG. 1 is a plant for carrying out a GTL process which converts a hydrocarbon feedstock such as a natural gas into liquid fuels.

The liquid fuel synthesizing system 1 is constituted with a synthesis gas production unit 3, an FT synthesis unit 5 and an upgrading unit 7. The synthesis gas production unit 3 reforms a natural gas that functions as a hydrocarbon feedstock to produce a synthesis gas containing carbon monoxide gas and hydrogen gas. The FT synthesis unit 5 synthesizes liquid hydrocarbons from the synthesis gas produced by the synthesis gas production unit 3 according to the FT synthesis reaction. The upgrading unit 7 hydrotreats the liquid hydrocarbons synthesized by the FT synthesis reaction to produce base stocks of liquid fuels (mainly kerosene and gas oil).

Structural elements of each of these units will be described below.

The synthesis gas production unit 3 mainly includes, for example, a desulfurization reactor 10, a reformer 12, a waste heat boiler 14, gas-liquid separators 16 and 18, a $CO_2$ removal unit 20, and a hydrogen separator 26. The desulfurization reactor 10 is composed of a hydrodesulfurizer and the like, and removes sulfur compounds from a natural gas that functions as the feedstock. The reformer 12 reforms the natural gas supplied from the desulfurization reactor 10 to produce a synthesis gas containing carbon monoxide gas (CO) and hydrogen gas ($H_2$) as main components. The waste heat boiler 14 recovers waste heat from the synthesis gas produced in the reformer 12 to generate a high-pressure steam.

The gas-liquid separator 16 separates the water that has been heated by heat exchange with the synthesis gas in the waste heat boiler 14 into a gas (high-pressure steam) and a liquid. The gas-liquid separator 18 removes a condensed component from the synthesis gas that has been cooled in the waste heat boiler 14, and supplies a gas component to the $CO_2$ removal unit 20. The $CO_2$ removal unit 20 is provided with an absorption tower 22 which uses an absorbent to remove carbon dioxide gas from the synthesis gas supplied from the gas-liquid separator 18 and a regeneration tower 24 which strips the carbon dioxide gas from the absorbent containing the carbon dioxide gas, thereby regenerating the absorbent. The hydrogen separator 26 separates a portion of hydrogen gas contained in the synthesis gas from which the carbon dioxide gas has been separated by the $CO_2$ removal unit 20. However, in some cases, the $CO_2$ removal unit 20 may not need to be provided.

In the reformer 12, for example, by utilizing a steam and carbon dioxide gas reforming method represented by the chemical reaction formulae (1) and (2) shown below, the natural gas is reformed by using carbon dioxide gas and steam, and a high-temperature synthesis gas is produced which includes carbon monoxide gas and hydrogen gas as main components. In addition, the reforming method employed in the reformer 12 is not limited to the example of steam and carbon dioxide gas reforming method. There may also be used, for example, a steam reforming method, a partial oxidation reforming method (PDX) using oxygen, an autothermal reforming method (ATR) that is a combination of a partial oxidation reforming method and a steam reforming method, or a carbon dioxide gas reforming method, and so on.

$$CH_4 + H_2O \rightarrow CO + 3H_2 \qquad (1)$$

$$CH_4 + CO_2 \rightarrow 2CO + 2H_2 \qquad (2)$$

Further, the hydrogen separator 26 is provided on a branch line that branches off a main line which connects the $CO_2$ removal unit 20 or the gas-liquid separator 18 with a slurry bubble column reactor 30. The hydrogen separator 26 may be composed, for example, of a hydrogen PSA (Pressure Swing Adsorption) device that performs adsorption and desorption of hydrogen by utilizing a pressure difference. This hydrogen PSA device has adsorbents (such as a zeolitic adsorbent, activated carbon, alumina or silica gel) packed inside a plurality of adsorption towers (not shown in the drawing) that are arranged in parallel. By sequentially repeating each of the steps of hydrogen pressurization, adsorption, desorption (depressurization) and purging within each of these adsorption towers, a high-purity hydrogen gas (of approximately 99.999% purity) that has been separated from the synthesis gas can be continuously supplied to various types of hydrogen utilizing reactors in which hydrogen is used to perform predetermined reactions (for example, the desulfurization reactor 10, a wax fraction hydrocracking reactor 60, a middle distillate hydrotreating reactor 61, a naphtha fraction hydrotreating reactor 62, and so on).

The hydrogen gas separating method employed in the hydrogen separator 26 is not limited to the type of pressure swing adsorption method utilized by the above hydrogen PSA device. For example, a hydrogen storing alloy adsorption method, a membrane separation method, or a combination thereof may also be used.

Figure 2:
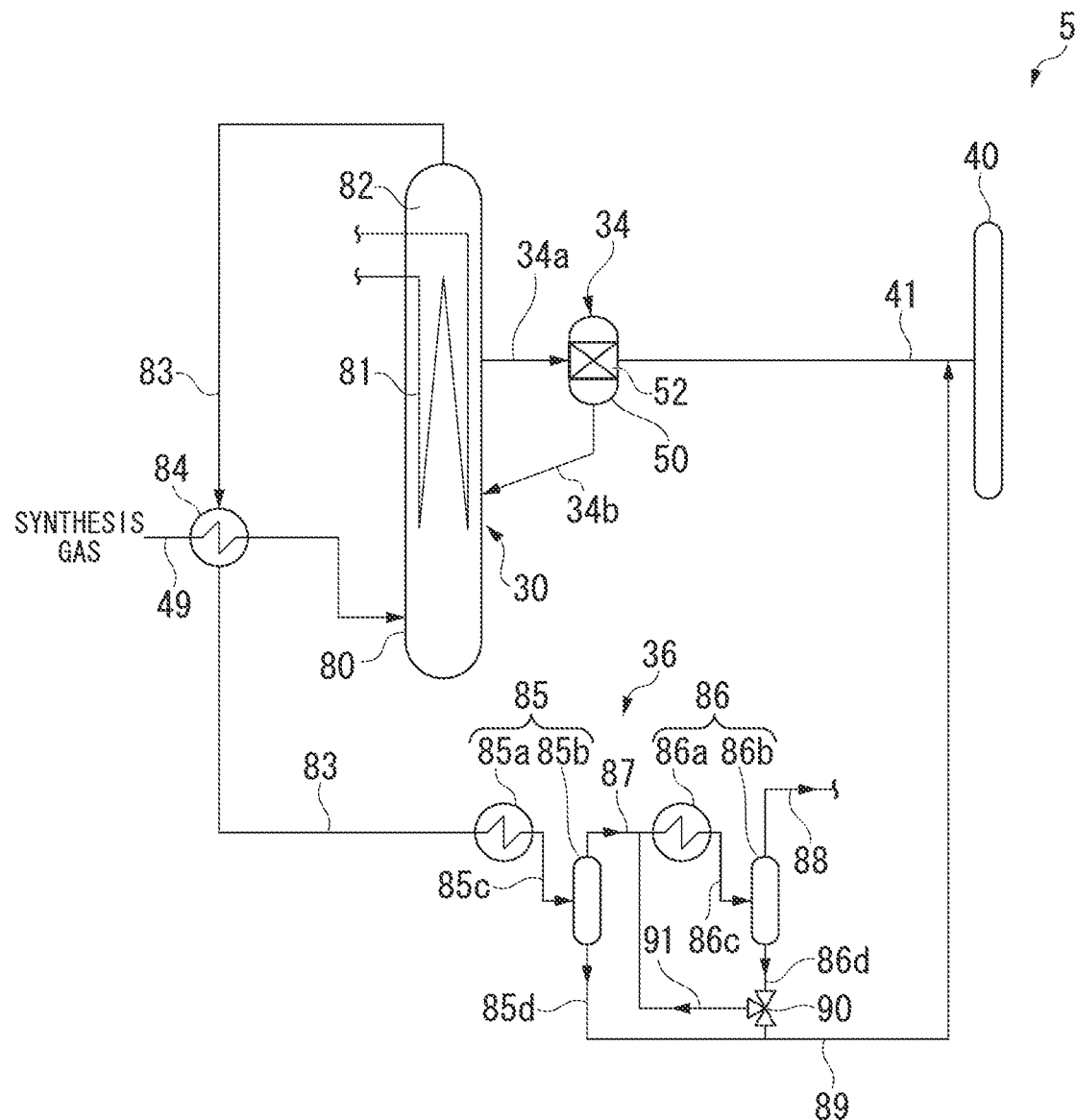
FIG. 2 is a schematic constitution diagram which shows an FT synthesis unit of the present invention.

Next, a description will be given about the FT synthesis unit 5 with reference to FIG. 1 and FIG. 2. As shown in FIG. 1 and FIG. 2, the FT synthesis unit 5 is mainly provided with a slurry bubble column reactor 30 (hereinafter, in some cases, referred to as a "reactor 30"), a gas-liquid separator 32, an external catalyst separator 34, a gas-liquid separator 36, and a first fractionator 40.

The reactor 30 synthesizes liquid hydrocarbons from the synthesis gas, functioning as an FT synthesis reactor which synthesizes the liquid hydrocarbons from the synthesis gas by the FT synthesis reaction. This reactor 30 is mainly provided with a reactor main unit 80 and a cooling line 81. The reactor 30 is operated under conditions, for example, an inner temperature of approximately 180 to 270° C. and a pressure higher than atmospheric pressure.

The reactor main unit 80 is a metal vessel which is formed approximately in a cylindrical shape. A slurry prepared by suspending solid catalyst particles in liquid hydrocarbons (products of the FT synthesis reaction) is contained inside the reactor main unit 80 to form a slurry bed.

The synthesis gas containing hydrogen gas and carbon monoxide gas as main components is to be injected into the slurry at a lower part of the reactor main unit 80. Then, the synthesis gas which has been blown into the slurry is formed into bubbles, ascending in the slurry from below to above in a direction of height of the reactor main unit 80 (in the perpendicular direction). In the course thereof, the synthesis gas is dissolved in liquid hydrocarbons and brought into contact with the catalyst particles, by which a synthesis reaction (the FT synthesis reaction) of the liquid hydrocarbons proceeds. More specifically, as expressed by the chemical reaction formula (3) shown below, hydrogen gas reacts with carbon monoxide gas to produce hydrocarbons.

$$2nH_2 + nCO \rightarrow (-CH_2-)_n + nH_2O \qquad (3)$$

Here, in the above reaction, a percentage of carbon monoxide gas consumed inside the reactor with respect to carbon monoxide gas (CO) supplied to the reactor is referred to as a reaction conversion ratio of carbon monoxide in the present application (hereinafter, in some cases, simply referred to as "reaction conversion ratio"). This reaction conversion ratio is calculated in terms of a percentage from a molar flow rate of carbon monoxide gas in a gas which flows into the reactor main unit 80 per unit time (inlet CO molar flow rate) and a molar flow rate of carbon monoxide gas in discharged gas components drawn out from a gas phase portion 82 of the reactor main unit 80 per unit time (outlet CO molar flow rate), as will be described later. That is, the reaction conversion ratio is obtained by the following formula (4).

Reaction conversion ratio = $\frac{(\text{inlet CO molar rate} - \text{outlet CO molar flow rate})}{\text{inlet CO molar flow rate}} \times 100$ (4)

In order to reuse the synthesis gas which is contained in the discharged gas components discharged from the gas phase portion of the reactor and which remains unreacted inside the reactor main unit 80, it is common practice that gas components obtained by cooling and condensing the discharged gas components and separated from liquid components are recycled into the reactor and provided again for reaction. In this case, the inlet CO molar flow rate is a molar flow rate of carbon monoxide gas which is contained in a gas at the inlet of the reactor and composed of a newly supplied synthesis gas and the recycle gas.

A molar flow rate of carbon monoxide gas in the synthesis gas which flows into the reactor main unit 80 per unit time (inlet CO molar flow rate) is continuously or regularly determined, for example, by gas chromatograph and a flow-meter (not shown in the drawing) installed on a supply line 49 which supplies the synthesis gas to the reactor main unit 80. As described above, where a gas containing the unreacted synthesis gas is recycled into the reactor main unit 80, the gas chromatograph and the flow-meter may be installed at such positions on the supply line 49 that are downstream from a converging point of the supply line 49 with a line through which the recycle gas is flowed. Further, a molar flow rate of carbon monoxide gas in the discharged components drawn out from the gas phase portion 82 of the reactor main unit 80 per unit time (outlet CO molar flow rate) is continuously or regularly determined by the gas chromatography and the flow-meter (not shown in the drawing) installed on a discharge line 88 to be described later. Therefore, a reaction conversion ratio of carbon monoxide is continuously or regularly calculated on the basis of the above-determined values and also on the basis of the formula (4). The operation is monitored by the result thereof.

Further, since the synthesis gas is formed into bubbles to ascend inside the reactor main unit 80, an ascending flow (air lift) of the slurry inside the reactor main unit 80 is generated. Thereby, the slurry circulates inside the reactor main unit 80.

The gas phase portion 82 is provided at the upper part of the slurry which is accommodated in the reactor main unit 80. Gas-liquid separation is carried out on an interface between the gas phase portion 82 and the slurry. That is, the synthesis gas which has remained unreacted in the slurry and passed over the interface between the slurry and the gas phase portion 82 and the relatively light hydrocarbons which are produced by the FT synthesis reaction and in a gaseous state under the conditions inside the reactor main unit 80 move to the gas phase portion 82 as gas components. At this time, droplets entrained with the gas components and catalyst particles entrained with the droplets are returned to the slurry by gravitational force. Then, the gas components (the unreacted synthesis gas and the light hydrocarbons) which have ascended up to the gas phase portion 82 of the reactor main unit 80 are drawn out via a line (discharge line 83) connected to the gas phase portion (the upper part) of the reactor main unit 80 and formed into discharged gas components. The discharged gas components are thereafter cooled in a manner to be described later and supplied to the gas-liquid separator 36.

The cooling line 81 is provided inside the reactor main unit 80, and maintains the temperature inside the system at a predetermined temperature by removing the heat of reaction generated by the FT synthesis reaction. This cooling line 81 may be formed, for example, by bending a single tube so that is runs up and down a plurality of times along the vertical direction. Further, a plurality of cooling lines having a so-called bayonet double-tube structure may also be installed inside the reactor main unit 80. In other words, the shape and number of cooling line 81 is not limited to the shape and number described above, and any structure that can be positioned inside the reactor main unit 80 and contributes to cooling of the slurry may be used.

The cooling line 81 is to flow cooling water (which is, for example, different in temperature from the interior of the reactor main unit 80 at approximately −50 to 0° C.) supplied from the gas-liquid separator 32 shown in FIG. 1. While the cooling water flows through the cooling line 81, heat exchange is performed between a tubular wall of the cooling line 81 and the slurry, by which the slurry inside the reactor main unit 80 is cooled. A portion of the cooling water is vaporized into steam, discharged into the gas-liquid separator 32 and recovered as a middle-pressure steam.

A medium for cooling the slurry shall not be limited to the above-described cooling water but may include, for example, linear, branched or cyclic alkane with a carbon number of $C_4$ to $C_{10}$, olefin, low-molecular weight silane, silyl ether, silicon oil, and so on.

The gas-liquid separator 32 separates water heated by flowing through the cooling line 81 disposed inside the reactor 30 into steam (middle-pressure steam) and a liquid. The liquid separated by the gas-liquid separator 32 is, as described above, again supplied to the cooling line 81 as cooling water.

Although a catalyst which constitutes the slurry contained in the reactor main unit 80 is not limited in particular, preferably used is a solid-particle catalyst in which at least one type of active metal selected from cobalt, ruthenium, iron, and so on, is supported on a carrier composed of an inorganic oxide such as silica and alumina. This catalyst may further contain metal components such as zirconium, titanium, hafnium, and rhenium added for enhancing activities of the catalyst, in addition to the active metal. The catalyst is not in particularly restricted by the shape but is preferably in a substantially spherical shape, in view of the fluidity of the slurry and in view of suppressing pulverization of catalyst particles by collapse or wear of the catalyst particles resulting from collision and friction between the catalyst particles as well as collision and friction of the catalyst particles with an inner wall of the reactor main unit 80, the cooling line 81, and so on.

Further, although the catalyst particles are not in particular restricted by an average particle size, the average particle size is preferably in a range of approximately 40 to 150 µm in view of the fluidity of the slurry.

As shown in FIG. 2, the external catalyst separator 34 is provided with a separation vessel 50 disposed outside the reactor 30 and a filter 52 installed inside the separation vessel 50. The filter 52 for catching catalyst particles to separate the catalyst particles from the liquid hydrocarbons which constitute the slurry is installed in a single stage or a multiple stage in a direction at which the slurry flows. An aperture of the filter (where the filter is installed in a multiple stage, an aperture of the smallest filter) is from 5 µm to 30 µm, preferably from 5 to 20 µm, and more preferably from 5 to 15 µm. Further, an outflow line 34a connected to a middle section of the reactor main unit 80 is installed at an upper part of the separation vessel 50, while a return line 34b connected to a lower part of the reactor main unit 80 is installed at a lower part of the separation vessel 50.

Here, the lower part of the reactor main unit 80 is a part covering the length range of ⅓ or less of the reactor main unit 80 from the bottom of the reactor main unit 80. The middle section of the reactor main unit 80 is a part between the upper part and the lower part of the reactor main unit 80. The outflow line 34a is a line for supplying a portion of the slurry inside the reactor main unit 80 to the external catalyst separator 34, while the return line 34b is a line for returning catalyst particles and hydrocarbon oils caught by the filter 52 to the reactor main unit 80.

Further, a line 41 is connected to the filter 52 inside the separation vessel 50, thereby discharging liquid hydrocarbons separated from the catalyst particles. Further, a filtering apparatus (not shown in the drawing) and a storage tank (not shown in the drawing) are disposed in this order on the line 41, whenever necessary. The filtering apparatus has a filter (not shown in the drawing) internally and filtrates the liquid hydrocarbons introduced by the filter. That is, the filter of the filtering device catches and removes at least a portion of the catalyst particles which have pulverized in the liquid hydrocarbons and flowed out without being caught by the filter 52.

The storage tank temporarily stores the liquid hydrocarbons filtrated by the filter 52 and again filtrated by the filtering device.

Then, after the filtering apparatus (not shown in the drawing) and the storage tank (not shown in the drawing) are disposed on the line 41 whenever necessary, the first fractionator 40 is connected further to the downstream side of the line 41.

Still further, a discharge line 83 is connected to the gas phase portion 82 (the top) of the reactor main unit 80 in the reactor 30. The discharge line 83 is connected via a heat exchange unit 84 to the gas-liquid separator 36 and transfers gas components in the gas phase portion 82 which have ascended up to the top of the reactor main unit 80 to the gas-liquid separator 36 as discharged gas components. The heat exchange unit 84 performs heat exchange between the synthesis gas supplied from the synthesis gas production unit 3 and the gas components drawn out from the reactor main unit 80, thereby heating the synthesis gas relatively low in temperature and also cooling the discharged gas components relatively high in temperature.

In the present embodiment, the gas-liquid separator 36 is composed of a first gas-liquid separating unit 85 and a second gas-liquid separating unit 86. The first gas-liquid separating unit 85 is arranged upstream to constitute a former stage, while the second gas-liquid separating unit 86 is arranged downstream to constitute a subsequent stage. Therefore, in the present embodiment, the second gas-liquid separating unit 86 acts as the last stage of the gas-liquid separating unit in the gas-liquid separator 36. The gas-liquid separator 36 of the present invention is not limited to a two-stage constitution but may be provided in a three-stage constitution or more or in a single stage constitution. The gas-liquid separator 36 is constituted in a multiple stage, by which liquefiable components (light liquid hydrocarbons) contained in the discharged gas components can be reliably liquefied and recovered. Where the gas-liquid separator 36 is constituted in a single stage, a single gas-liquid separating unit acts as the last stage of the gas-liquid separating unit of the gas-liquid separator 36 in the present invention.

The first gas-liquid separating unit 85 is composed of a first cooler 85a and a first gas-liquid separation vessel 85b disposed downstream from the first cooler 85a. The second gas-liquid separating unit 86 is composed of a second cooler 86a and a second gas-liquid separation vessel 86b disposed downstream from the second cooler 86a. The first cooler 85a of the first gas-liquid separating unit 85 is directly connected to the discharge line 83 and performs heat exchange between discharged components cooled through the heat exchange unit 84 and a coolant such as water, thereby facilitating cooling, with a portion of the discharged components being liquefied. For example, the first cooler 85a is constituted so as to make a temperature at the outlet thereof to be approximately 110° C. by further cooling the discharged components which have been cooled through the heat exchange unit 84. The first gas-liquid separation vessel 85b is connected to the outlet of the first cooler 85a via a first line 85c and separates liquid hydrocarbons having boiling points in excess of approximately 110° C. from gas components having boiling points lower than approximately 110° C., thereby discharging the gas components into the second gas-liquid separating unit 86 side.

The second cooler 86a of the second gas-liquid separating unit 86 is connected to the top of the first gas-liquid separation vessel 85b via a connection line 87 and performs heat exchange between the gas components drawn out from the first gas-liquid separation vessel 85b and a coolant such as water to facilitate cooling, with a portion of the gas components being liquefied. For example, the second cooler 86a is constituted so as to make the temperature at the outlet thereof to be approximately 35° C. to 40° C. by further cooling the gas components which have been drawn out from the first gas-liquid separation vessel 85b. The second gas-liquid separation vessel 86b is connected to the outlet of the second cooler 85a via a second line 86c and separates liquid hydrocarbons having boiling points in excess of approximately 35° C. to 40° C. from gas components having boiling points lower than 35° C. to 40° C., thereby discharging the gas components through the discharge line 88 installed at the top.

The gas components discharged from the discharge line 88 mainly contain unreacted synthesis gases (CO, $H_2$) and gaseous hydrocarbons with a carbon number of $C_4$ or less. It is common practice that, during normal operation, the gas components discharged from the second gas-liquid separation vessel 86b are partially or entirely returned through a recycle line (not shown in the drawing) to the supply line 49 of the synthesis gas and supplied again for the FT synthesis reaction, together with newly supplied synthesis gas. Further, the gas components discharged from the discharge line 88 may be flared partially or entirely as flare gas.

The second line 86c is provided with a temperature sensor (not shown in the drawing), by which a temperature at the outlet of the second cooler 86a is continuously monitored.

A first discharge line 85d for discharging the liquid hydrocarbons separated from the gas components is connected to the bottom of the first gas-liquid separation vessel 85b, while a second discharge line 86d for discharging the liquid hydrocarbons separated from the gas components is connected to the bottom of the second gas-liquid separation vessel 86b. The first discharge line 85d and the second discharge line 86d are connected to a single line 89, and this line 89 is connected to the line 41.

The first fractionator 40 is disposed by being connected to the line 41, distilling heavy liquid hydrocarbons supplied through the line 41, that is, liquid hydrocarbons discharged from the external catalyst separator 34 and light liquid hydrocarbons supplied through the first discharge line 85d, the second discharge line 86d and the line 89, that is, liquid hydrocarbons discharged from the first gas-liquid separation vessel 85b and the second gas-liquid separation vessel 86b, thereby separating them into each fraction depending on the boiling points.

However, in the present embodiment, a switching valve 90 composed of a three-way valve, and so on, is installed on the second discharge line 86d which is a downstream side line of the second gas-liquid separating unit 86 acting as the last stage of the gas-liquid separating unit of the gas-liquid separator 36. A light liquid hydrocarbon supply line 91 is connected to the switching valve 90. In the present embodiment, the light liquid hydrocarbon supply line 91 is connected to a line which is positioned just before the second gas-liquid separating unit 86 (the last stage of the gas-liquid separating unit of the gas-liquid separator 36), that is, a connection line 87 positioned just before the second cooler 86a. Then, the light liquid hydrocarbon supply line 91 is provided, for example, with a pump (not shown in the drawing), thereby supplying the light liquid hydrocarbons flowing through the second discharge line 86d to the connection line 87. That is, the light liquid hydrocarbon supply line 91 is connected at one end to the second discharge line 86d and at the other end to the connection line 87.

Here, the light liquid hydrocarbons discharged into the second discharge line 86d which is a downstream side line of the second gas-liquid separating unit 86 (the last stage of the gas-liquid separating unit of the gas-liquid separator 36) are liquid hydrocarbons condensed at the second cooler 86a, that is, light hydrocarbons having cloud points (CP) specified by the JIS K2269 lower than a temperature at the outlet of the second cooler 86a in the second gas-liquid separating unit 86 (approximately 35° C. to 40° C. during normal operation). The light hydrocarbons flowing through the line 89 are also light hydrocarbons having cloud points lower than the temperature at the outlet of the second cooler 86a.

The switching valve 90 can be changed three ways, that is, a mode in which the entire quantity of the light liquid hydrocarbons discharged from the second gas-liquid separation vessel 86b are discharged into the line 89, a mode in which the entire quantity are discharged into the light liquid hydrocarbon supply line 91, and a mode in which a portion are discharged into the line 89 and the remainder are discharged into the light liquid hydrocarbon supply line 91. Further, in the mode in which some of the light liquid hydrocarbons are discharged into the line 89 and the remainder are discharged into the light liquid hydrocarbon supply line 91, the ratio of the light liquid hydrocarbons discharged into each of the lines 89, 91 can be adjusted in quantity, whenever necessary.

As shown in FIG. 1, the upgrading unit 7 is provided, for example, with a wax fraction hydrocracking reactor 60, a middle distillate hydrotreating reactor 61, a naphtha fraction hydrotreating reactor 62, gas-liquid separators 63, 64, 65, a second fractionator 70, and a naphtha stabilizer 72. The wax fraction hydrocracking reactor 60 is connected to the bottom of the first fractionator 40. The middle distillate hydrotreating reactor 61 is connected to the middle section of the first fractionator 40. The naphtha fraction hydrotreating reactor 62 is connected to the upper part of the first fractionator 40. The gas-liquid separators 63, 64, 65 are installed so as to correspond respectively to hydrogenation reactors 60, 61, 62. The second fractionator 70 fractionally distills the liquid hydrocarbons supplied from the gas-liquid separators 63, 64, depending on the boiling points. The naphtha stabilizer 72 fractionates the liquid hydrocarbons of a naphtha fraction supplied from the gas-liquid separator 65 and the second fractionator 70, thereby discharging gas components with a carbon number of $C_4$ or less as a flare gas and recovering components with a carbon number of 5 or more as products of the naphtha fraction.

The above-constituted upgrading unit 7 is basically on a downstream side line of the second gas-liquid separating unit 86 of the gas-liquid separator 36 (the last stage of the gas-liquid separating unit of the gas-liquid separator 36). Then, for example, hydrocarbons flowing through a line 75a which connects the first fractionator 40 with the middle distillate hydrotreating reactor 61, a line 75b which connects the first fractionator 40 with the naphtha fraction hydrotreating reactor 62, a line 75d which is connected to the bottom of the gas-liquid separator 64, a line 75e which is connected to the bottom of the gas-liquid separator 65, lines 75f and 75g which are connected to the second fractionator 70, and a line 75h which is connected to the bottom of the naphtha stabilizer 72 are also changed into light hydrocarbons having cloud points normally lower than a temperature at the outlet of the second cooler 86a (approximately 35° C. to 40° C. during normal operation). Hydrocarbons flowing through a line 75c which is connected to the bottom of the gas-liquid separator 63 may also meet the above requirements, depending on operating conditions of the wax fraction hydrocracking reactor 61.

Next, a description will be given of a step (GTL process) for synthesizing liquid fuels from a natural gas by using the synthesis reaction system 1 which is constituted as described above.

The synthesis reaction system 1 is supplied with a natural gas (main component is $CH_4$) as a hydrocarbon feedstock from an external natural gas source (not shown in the drawing) such as a natural gas field or a natural gas plant. The synthesis gas production unit 3 reforms the natural gas to produce a synthesis gas (a mixed gas having carbon monoxide gas and hydrogen gas as main components).

First, the natural gas is supplied to a desulfurization reactor 10, together with hydrogen gas separated by the hydrogen separator 26. The desulfurization reactor 10 uses the hydrogen gas to hydrogenate sulfur compounds contained in the natural gas with a known desulfurization catalyst to hydrogen sulfide. Further, the hydrogen sulfide is adsorbed and removed by using an adsorbent such as zinc oxide to desulfurize the natural gas. The natural gas is in advance subjected to desulfurization in the manner described above, by which catalysts used in the reformer 12, the slurry bubble column reactor 30, the upgrading unit 7, and so on, can be prevented from being reduced in activities by sulfur compounds.

The thus desulfurized natural gas (which may contain carbon dioxide gas) is supplied to the reformer 12 after carbon dioxide gas ($CO_2$) supplied from a carbon dioxide gas source (not shown in the drawing) has been mixed with steam generated by the waste heat boiler 14. The reformer 12 uses carbon dioxide gas and steam to reform the natural gas, thereby producing a high-temperature synthesis gas containing carbon monoxide gas and hydrogen gas as main components, for example, by a steam and carbon dioxide gas reforming method. At this time, the reformer 12 is supplied, for example, with a fuel gas and air for a burner equipped in the reformer 12. Combustion heat of the fuel gas from the burner and radiation heat inside a furnace of the reformer 12 provide reaction heat necessary for the steam and carbon dioxide gas reforming reaction which is an endothermic reaction.

The high-temperature synthesis gas (for example, 900° C. and 2.0 MPaG) produced by the reformer 12 as described above is supplied to the waste heat boiler 14, cooled (for example, 400° C.) by heat exchange with water which flows inside the waste heat boiler 14 and recovered for waste heat. At this time, the water heated by the synthesis gas at the waste heat boiler 14 is supplied to the gas-liquid separator 16, and gas components are supplied from the gas-liquid separator 16 as a high-pressure steam (for example, 3.4 to 10.0 MPaG) to the reformer 12 or other external equipment. Water which is a liquid component is returned to the waste heat boiler 14.

On the other hand, the synthesis gas cooled by the waste heat boiler 14 is supplied to an absorption tower 22 of the $CO_2$ removal unit 20 or a slurry bubble column reactor 30, after condensed liquid components have been separated and removed by the gas-liquid separator 18. The absorption tower 22 absorbs carbon dioxide gas contained in the synthesis gas into a contained absorbent, thereby separating carbon dioxide gas from the synthesis gas. The absorbent inside the absorption tower 22 which contains the carbon dioxide gas is introduced into the regeneration tower 24. Also, the absorbent which contains the carbon dioxide gas is heated by steam, for example, and subjected to stripping treatment. The thus stripped carbon dioxide gas is brought from the regeneration tower 24 to the reformer 12 and reused for the reforming reaction.

The synthesis gas produced by the synthesis gas production unit 3 as described above is supplied via the supply line 49 shown in FIG. 2 to the slurry bubble column reactor 30 of the FT synthesis unit 5. At this time, a composition ratio of the synthesis gas supplied to the slurry bubble column reactor 30 is adjusted to a composition ratio suitable for the FT synthesis reaction (for example, $H_2:CO=2:1$ (molar ratio)). In the present embodiment, this synthesis gas acts as a coolant for cooling in the heat exchange unit 84 the gas components drawn out from a gas phase portion of the slurry bubble column reactor 30. Therefore, the synthesis gas may be constituted so that preliminary cooling can be provided, whenever necessary, for cooling the gas components to a desired temperature. Further, the synthesis gas may be constituted so as to be pressurized to a pressure appropriate for the FT synthesis reaction (for example, 3.6 MPaG) by a compressor (not shown in the drawing) installed on a line connecting the $CO_2$ removal unit 20 with the slurry bubble column reactor 30.

Further, a portion of the synthesis gas from which carbon dioxide gas has been separated by the $CO_2$ removal unit 20 is also supplied to the hydrogen separator 26. The hydrogen separator 26 separates hydrogen gas contained in the synthesis gas through adsorption and desorption (hydrogen PSA) utilizing a difference in pressure as described above. The separated hydrogen gas is continuously supplied from a gas holder (not shown in the drawing) or the like via a compressor (not shown in the drawing) to various types of hydrogen utilizing reactors (for example, the desulfurization reactor 10, the wax fraction hydrocracking reactor 60, the middle distillate hydrotreating reactor 61, the naphtha fraction hydrotreating reactor 62, and so on) in which the hydrogen gas is used to conduct predetermined reactions inside the synthesis reaction system 1.

Next, the FT synthesis unit 5 synthesizes hydrocarbons from the synthesis gas produced by the synthesis gas production unit 3 according to the FT synthesis reaction. Hereinafter, a description will be given about one embodiment of the hydrocarbon production process of the present invention on the basis of a process for synthesizing hydrocarbons by the FT synthesis reaction.

During normal operation of the FT synthesis unit 5, the synthesis gas produced by the synthesis gas production unit 3 is supplied through the supply line 49 and converged into the supply line 49 through a recycle line (not shown in the drawing). After being mixed with a recycle gas containing the synthesis gas which has remained unreacted in the reactor 30, the synthesis gas is heated in the heat exchange unit 84 by heat exchange with discharged gas components drawn out from the reactor 30, flowing from the bottom of the reactor main unit 80 constituting the slurry bubble column reactor 30, and ascending inside a slurry retained in the reactor main unit 80 as gas bubbles. At this time, carbon monoxide gas and hydrogen gas contained in the synthesis gas undergo reaction by the above-described FT synthesis reaction to produce hydrocarbons in the reactor main unit 80. As described above, a mixed gas of the synthesis gas supplied through the supply line 49 with the recycle gas is determined for its flow rate by a flow-meter (not shown in the drawing) prior to flowing into the reactor main unit 80. Further, gas chromatograph (not shown in the drawing) is used to determine the concentration of carbon monoxide gas contained in the mixed gas. Then, these values are referenced to calculate a molar flow rate (inlet CO molar flow rate) of carbon monoxide gas which flows into the reactor main unit 80 per unit time.

Further, at the time of this synthesis reaction, water is flowed through the cooling line 81 to remove the reaction heat of the FT synthesis reaction. The water heated by the heat exchange is vaporized into steam. Water which is a liquid contained in this steam is separated by the gas-liquid separator 32 and returned to the cooling line 81, and gas components are supplied to external equipment as a middle-pressure steam (for example, 1.0 to 2.5 MPaG).

A portion of the slurry which contains liquid hydrocarbons and catalyst particles in the reactor main unit 80 of the bubble column reactor 30 is, as shown in FIG. 2, drawn out from the middle section of the reactor main unit 80 via the outflow line 34a and introduced into the external catalyst separator 34. In the external catalyst separator 34, the introduced slurry is filtrated through a filter 52 to catch the catalyst particles. Thereby, the slurry is separated into solid components and liquid components composed of liquid hydrocarbons. In order to remove the caught catalyst particles from the surface of the filter and return them to the reactor main unit 80, hydrocarbon oil is flowed to the filter 52 of the external catalyst separator 34, whenever necessary, in a direction opposite to a normal flow direction. At this time, the catalyst particles caught by the filter 52 are returned via the return line 34b to the reactor main unit 80, together with a portion of the liquid hydrocarbons.

Further, the discharged gas components which have been drawn out from the gas phase portion 82 of the reactor main unit 80 are cooled by heat exchange with the synthesis gas (containing recycle gas) supplied to the reactor main unit 80 at the heat exchange unit 84 through the discharge line 83 and, thereafter, flow into the gas-liquid separator 36. The gas components flowing through the discharge line 88 for discharging the gas components from the gas-liquid separator 36 are, as described above, determined for the flow rate by the flow-meter, and carbon monoxide gas contained therein is determined for the concentration by the gas chromatography. These values are referenced to calculate a molar flow rate (outlet CO molar flow rate) of carbon monoxide gas drawn out per unit time from the discharge line 83 which is connected to the top of the reactor main unit 80. Thereby, the reactor 30 is continuously or regularly calculated and monitored for a reaction conversion ratio.

During normal operation of the FT synthesis unit 5, the reaction conversion ratio is from approximately 50% to 90%, and there is no case that the reaction conversion ratio is less than 20% except for the start-up of starting the supply of synthesis gas or the other occasions of unsteady operation.

Gas components which have been discharged from the top of the reactor main unit 80 and flowed into the gas-liquid separator 36 are further cooled by the first cooler 85a of the first gas-liquid separating unit 85, flowing into the first gas-liquid separation vessel 85b in a gas-liquid mixture state. Gas-liquid mixture products which have flowed into the first gas-liquid separation vessel 85b are here subjected to gas-liquid separation. Also, liquid components, that is, light liquid hydrocarbons are discharged from the first discharge line 85d.

Further, gas components which have flowed into the first gas-liquid separation vessel 85b and have been separated from the liquid components into gas and liquid and thereafter flowed through the connection line 87 are further cooled by the second cooler 86a of the second gas-liquid separating unit 86, flowing into the second gas-liquid separation vessel 86b in a gas-liquid mixture state. Gas-liquid mixture products which have flowed into the second gas-liquid separation vessel 86b are here subjected to gas-liquid separation. Liquid components, that is, light liquid hydrocarbons are discharged from the second discharge line 86d. During normal operation of the FT synthesis unit 5, the switching valve 90 installed on the second discharge line 86d is in a mode to discharge all the light liquid hydrocarbons flowing through the second discharge line 86d into the line 89.

Therefore, the light liquid hydrocarbons flowing through the second discharge line 86d flow into the line 89 in a similar manner as the light liquid hydrocarbons flowing through the first discharge line 85d, thereafter, flowing into the first fractionator 40 through the line 41. The gas components which have been separated by the second gas-liquid separation vessel 86b are discharged from the discharge line 88 as described above. Further, water which is a by-product in the reactor 30 is contained in liquid components flowing into the second gas-liquid separation vessel 86b. Therefore, it is preferable to install a drain line (not shown in the drawing) at the bottom of the second gas-liquid separation vessel 86b.

The gas components which have been separated from the liquid components and discharged into the discharge line 88 in the gas-liquid separator 86b have, as described above, the synthesis gas unreacted in the reactor main unit 80 and gaseous hydrocarbons with a carbon number of C4 or less produced by the FT synthesis reaction as main components. During normal operation of the FT synthesis unit 5, the gas components are supplied through the recycle line (not shown in the drawing) to the supply line 49 of the synthesis gas, mixed with a newly supplied synthesis gas and recycled into the reactor main unit 80. The unreacted synthesis gas is again supplied for the FT synthesis reaction.

Further, at least a portion of the gas components discharged through the discharge line 88 may be flared as a flare gas.

On the other hand, where temporary stop of the FT synthesis reaction is required due to some reason or the like, for example, in the above-described preliminary stage of start-up, operation may be performed in such a manner that nitrogen gas is recycled inside the reaction system, with no synthesis gas (feedstock gas) being supplied as described above. Further, in an intermediate stage, for example, where operation is shifted from recycling of the nitrogen gas to normal operation, a reaction temperature is set to be lower than a temperature at which normal operation is performed, while synthesis gas is being supplied, by which the FT synthesis reaction is not substantially proceeded. Alternatively, there is a case where operation is performed at a reaction conversion ratio of carbon monoxide gas which is substantially lower than during normal operation.

During such unsteady operation, there is a case where wax is adhered and accumulated to a cooler of the gas-liquid separator 36, in particular, the second cooler 86a of the latter stage (last stage) of the second gas-liquid separating unit 86 to result in reduced heat conduction. In addition, a temperature at the outlet of the cooler rises beyond a temperature of normal operation (approximately 35° C. to 40° C.). The present inventor has assumed causes of the adhesion of wax inside the cooler as follows: As described above, during normal operation of the FT synthesis unit 5, a large quantity of the light liquid hydrocarbons condensed by the cooler flow inside the cooler However, in a case where the FT synthesis reaction is not substantially proceeded, or where a reaction conversion ratio is substantially reduced during the above unsteady operation, the quantity of the light liquid hydrocarbon flowing inside the cooler may be substantially reduced, and the reduction of the quantity of the light liquid hydrocarbon may result in reduced an efficiency of "washing away" the adhered wax.

Therefore, in the present embodiment, where operation is performed so that the FT synthesis reaction is not substantially proceeded in the reactor 30 or where operation is performed at a reaction conversion ratio which is 20% or less, the switching valve 90 installed on the second discharge line 86d is switched. Thereby, the light liquid hydrocarbons flowing through the second discharge line 86d are flowed partially or entirely into a light liquid hydrocarbon supply line 91. The quantity of the light liquid hydrocarbons which are flowed into the light liquid hydrocarbon supply line 91 are determined, whenever necessary, by referring to the conversion ratio, for example. That is, a quantity that the switching valve 90 is adjusted in such a manner that a sufficient washing-away effect can be obtained for the wax adhered and accumulated on the second cooler 86a.

The switching valve 90 is switched as described above, by which the light liquid hydrocarbons are flowed into the light liquid hydrocarbon supply line 91 in a predetermined quantity and also flowed into a connection line 87 positioned just before the second cooler 86a through the light liquid hydrocarbon supply line 91. Then, the light liquid hydrocarbons are again flowed through the second cooler 86a after passing through the connection line 87. Cloud points (CP) of the light liquid hydrocarbons passing through the light liquid hydrocarbon supply line 91 and flowing through the second cooler 86a are lower than a temperature at the outlet of the second cooler 86a. Therefore, there is no case that the wax in the light liquid hydrocarbons will be deposited at the above temperature and the wax adhered to the second cooler 86a can be again dissolved with the light liquid hydrocarbons and washed away. It is also possible to prevent wax from adhering to the second cooler 86a in the future.

Next, a description is given about a period during which the light liquid hydrocarbons are supplied to the connection line 87 from the light liquid hydrocarbon supply line 91 by exemplifying start-up of the FT synthesis unit 5 in the present embodiment.

At start-up of the FT synthesis unit 5, as a preliminary stage of supplying a feedstock gas (synthesis gas) to the reactor 30, nitrogen gas is normally recycled inside a system of the reactor 30 which retains a slurry, thereby securing the fluidity of the slurry. In this stage, although the FT synthesis reaction is not proceeded, some of heavy hydrocarbons contained in liquid hydrocarbons constituting the slurry are vaporized and discharged together with gas components having nitrogen gas discharged through the discharge line 83 from the top of the reactor main unit 80 as a main component. As the liquid hydrocarbons constituting the slurry at the start-up, heavy hydrocarbons substantially free of light hydrocarbons are generally used. Therefore, the light hydrocarbons vaporized from the liquid hydrocarbons and discharged through the discharge line 83 are small in quantity and the light liquid hydrocarbons condensed in the cooler are accordingly small in quantity. Thus, in operation for cycling the nitrogen gas, wax will easily adhere to the cooler. In order to prevent wax from adhering to the cooler, during operation of cycling the nitrogen gas, the light liquid hydrocarbons which have been in advance fed into the second gas-liquid separation vessel 86b through the light liquid hydrocarbon supply line 91 may be supplied to the connection line 87.

At the start-up of the FT synthesis unit 5, the supply of synthesis gas to the reactor 30 is then started. In general, even if the supply of synthesis gas starts, a reaction conversion ratio is not immediately set to be a value for normal operation. Instead, operation is performed so as to gradually increase the reaction conversion ratio. Even in this stage, newly produced hydrocarbons are significantly lower in quantity compared with normal operation. Further, since the reaction temperature is set to be low, hydrocarbons with a larger carbon number are produced (heavy hydrocarbons are produced in a relatively large quantity) due to characteristics of the FT synthesis reaction. Therefore, in a period during which the operation is performed in the above manner as well, wax will easily adhere to the cooler of the gas-liquid separator 36. In order to prevent wax from adhering to the cooler during this period, the light liquid hydrocarbons which have been fed in advance into the second gas-liquid separation vessel 86b from the light liquid hydrocarbon supply line 91 may be supplied to the connection line 87.

In general, the adhesion of wax to the cooler of the gas-liquid separator 36 is found in a period during which the FT synthesis reaction is not substantially proceeded and a period during which the reaction conversion ratio is 20% or less. In addition, the wax is easily adhered particularly in a period during which the FT synthesis reaction is not substantially proceeded and a period during which the reaction conversion ratio is 10% or less. Therefore, in the present embodiment, a period during which the light liquid hydrocarbons are supplied through the light liquid hydrocarbon supply line 91 to the connection line 87 is preferably a period during which the FT synthesis reaction is not substantially proceeded and a period during which the reaction conversion ratio is 20% or less, and in particular, preferably a period during which the FT synthesis reaction is not substantially proceeded and a period during which the reaction conversion ratio is 10% or less.

The light liquid hydrocarbons may be supplied from the light liquid hydrocarbon supply line 91 to the connection line 87 at any period as long as it is within the above mentioned periods. For example, upon start of initial operation, light liquid hydrocarbons are not supplied while a temperature at the outlet of the cooler 86a is monitored, and the supply of light liquid hydrocarbons may be started in a stage where the temperature is found to rise. Alternatively, in a stage where the nitrogen gas is recycled, the supply of light liquid hydrocarbons is started and, thereafter, the supply of synthesis gas is started to increase a reaction conversion ratio. In addition, the supply is continued until the reaction conversion ratio reaches 20%, during which the light liquid hydrocarbon may be supplied. The embodiment is carried out in the manner as described above, by which it is possible to most reliably prevent the adhesion of wax to the cooler. Alternatively, in a stage where the reaction conversion ratio reaches, for example, 10%, the supply of light liquid hydrocarbons may be stopped. Depending on the case, even in a stage where the reaction conversion ratio is in excess of 20%, the supply of light liquid hydrocarbons may be continued. However, in general, when the reaction conversion ratio is in excess of 20%, wax will not adhere to the cooler, even if the supply of light liquid hydrocarbons is stopped. This is assumed due to the fact that light hydrocarbons are produced in a larger quantity by the FT synthesis reaction and condensed inside the cooler and the light liquid hydrocarbons flowing inside the cooler are increased in quantity to provide a sufficient "washing-away" effect.

The light liquid hydrocarbons are supplied by the light liquid hydrocarbon supply line 91 to the connection line 87 in the manner described above by monitoring continuously or regularly a reaction conversion ratio in the reactor 30, and the supply of light liquid hydrocarbons can be continued or stopped depending on the reaction conversion ratio, as described above. Further, the supply of light liquid hydrocarbons may be continued or stopped by monitoring a temperature at the outlet of the cooler 86*a*.

In the present embodiment, the light liquid hydrocarbon supply line 91 is connected at the one end to the second discharge line 86*d* of the second cooler 86*a* and connected at the other end to the connection line 87, to which the present invention shall not be, however, limited. The one end of the light liquid hydrocarbon supply line 91 may be connected to a downstream side line from the second gas-liquid separating unit 86, while the other end thereof may be connected to an upstream side line from the second gas-liquid separating unit 86.

More specifically, as described above, the hydrocarbons flowing through the line 75*a* which connects the first fractionator 40 with the middle distillate hydrotreating reactor 61 in the upgrading unit 7, the line 75*b* which connects the first fractionator 40 with the naphtha fraction hydrotreating reactor 62, the line 75*d* which is connected to the bottom of the gas-liquid separator 64, the line 75*e* which is connected to the bottom of the gas-liquid separator 65, the lines 75*f* and 75*g* which are connected to the second fractionator 70, and the line 75*h* which is connected to the bottom of the naphtha stabilizer 72 are normally light hydrocarbons having cloud points lower than the temperature at the outlet of the second cooler 86*a* (approximately 35° C. to 40° C. during normal operation). The hydrocarbons flowing through the line 75*c* which is connected to the bottom of the gas-liquid separator 63 are also able to meet the requirements depending on the operating conditions of the wax fraction hydrocracking reactor 61. Therefore, one end of the light liquid hydrocarbon supply line 91 may be connected to any one or a plurality of the line 75*a* to the line 75*h*. Depending on the case, corresponding light liquid hydrocarbons may be accepted from an external source and one end of the light liquid hydrocarbon supply line 91 may be connected to an outlet line of a storage tank which accepted the light liquid hydrocarbons.

Further, the other end of the light liquid hydrocarbon supply line 91 may be connected to the discharge line 83, inside the reactor 30, or further to a line (upstream side line) of the supply line 49, for example, of synthesis gas.

The above constitution makes it possible to supply the light hydrocarbons having cloud points lower than a temperature at the outlet of the second cooler 86*a* to the upstream side of the second cooler 86*a*. Therefore, it is possible to prevent the adhesion of wax inside the second cooler 86*a* and also remove the adhered wax.

A temperature at the outlet of the second cooler 86*a* can be monitored continuously, for example, by a temperature sensor (not shown in the drawing) installed on the second line 86*c*. Time for starting to supply the light liquid hydrocarbons to the upstream side line may be judged by referring to the temperature at the outlet. Further, where the light liquid hydrocarbons to be supplied are selected on supplying the light liquid hydrocarbons to the upstream side line, it is preferable to supply the light liquid hydrocarbons having cloud points lower than the temperature at the outlet thereof compared with the temperature at the outlet thereof. Still further, where the light liquid hydrocarbons are supplied to the upstream side line, the effect can also be judged by the temperature at the outlet thereof, and the light liquid hydrocarbons to be supplied can be adjusted for the flow rate accordingly. In addition, it is preferable that the light liquid hydrocarbons now in supply are determined for cloud points to confirm that cloud points are lower than the temperature at the outlet thereof.

Next, in the first fractionator 40, the heavy liquid hydrocarbons supplied from the reactor 30 via the external catalyst separator 34 and the light liquid hydrocarbons supplied via the gas-liquid separator 36 in the manner described above are fractionally distilled and separated into a naphtha fraction (with a boiling point that is lower than approximately 150° C.), a middle distillate (with a boiling point of approximately 150 to 360° C.) and a wax fraction (with a boiling point that exceeds approximately 360° C.). The liquid hydrocarbons of the wax fraction (mainly $C_{22}$ or higher) obtained from the bottom of the first fractionator 40 are transferred to the wax fraction hydrocracking reactor 60. The liquid hydrocarbons of the middle distillate (mainly $C_{11}$ to $C_{21}$) obtained from the middle section of the first fractionator 40 are transferred to the middle distillate hydrotreating reactor 61. The liquid hydrocarbons of the naphtha fraction (mainly $C_5$ to $C_{10}$) obtained from the top of the first fractionator 40 are transferred to the naphtha fraction hydrotreating reactor 62.

The wax fraction hydrocracking reactor 60 hydrocracks the liquid hydrocarbons of the large-carbon number wax fraction (hydrocarbons of approximately $C_{22}$ or higher) supplied from the bottom of the first fractionator 40 by using the hydrogen gas supplied from the hydrogen separator 26 to reduce the carbon number to $C_{21}$ or less. In this hydrocracking reaction, C—C bonds of hydrocarbons with a large carbon number are cleaved by utilizing a catalyst and heat to produce low-molecular weight hydrocarbons with a small carbon number. Products containing the liquid hydrocarbons hydrocracked by the wax fraction hydrocracking reactor 60 are separated into a gas and a liquid in the gas-liquid separator 63, of which the liquid hydrocarbons are transferred to the second fractionator 70, and the gas components (including the hydrogen gas) are transferred to the middle distillate hydrotreating reactor 61 and the naphtha fraction hydrotreating reactor 62.

In the middle distillate hydrotreating reactor 61, the liquid hydrocarbons of the middle distillate which have a middle-range carbon number (of approximately $C_{11}$ to $C_{21}$) and which have been supplied from the middle section of the first fractionator 40 are hydrotreated by using the hydrogen gas supplied from the hydrogen separator 26 via the wax fraction hydrocracking reactor 60. In this hydrotreating reaction, mainly for the purpose of improving the low temperature fluidity of the fuel oil base stock, the liquid hydrocarbons are hydroisomerized for obtaining branched saturated hydrocarbons and hydrogen is added to unsaturated hydrocarbons contained in the liquid hydrocarbons to be saturated. Further, oxygen-containing compounds such as alcohols contained in the hydrocarbons are hydrogenated and converted to saturated hydrocarbons. Products containing the liquid hydrocarbons hydrotreated in the manner described above are separated into a gas and a liquid by the gas-liquid separator 64, of which the liquid hydrocarbons are transferred to the second fractionator 70 and the gas components (including the hydrogen gas) are reused in the hydrogenation reaction.

In the naphtha fraction hydrotreating reactor 62, the liquid hydrocarbons of the naphtha fraction which have a low carbon number (approximately $C_{10}$ or less) and which have been supplied from the upper part of the first fractionator 40 are hydrotreated by using the hydrogen gas supplied from the hydrogen separator 26 via the wax fraction hydrocracking reactor 60. Thereby, unsaturated hydrocarbons contained in the supplied naphtha fraction and oxygen-containing compounds such as alcohols are converted to saturated hydrocarbons. Products containing the liquid hydrocarbons hydrotreated in the manner described above are separated into a gas and a liquid by the gas-liquid separator 65, of which the liquid hydrocarbons are transferred to the naphtha stabilizer 72 and the gas components (including the hydrogen gas) are reused in the hydrogenation reaction.

Next, in the second fractionator 70, the liquid hydrocarbons hydrocracked and hydrotreated respectively in the wax fraction hydrocracking reactor 60 and the middle distillate hydrotreating reactor 61 are fractionally distilled into hydrocarbons with a carbon number of $C_{10}$ or less (with boiling points of approximately 150° C. or lower), a kerosene fraction (with a boiling point of approximately 150 to 250° C.), a gas oil fraction (with a boiling point of approximately 250 to 360° C.) and an uncracked wax fraction (with a boiling point exceeding approximately 360° C.) from the wax fraction hydrocracking reactor 60 as described above. The gas oil fraction is obtained from the lower part of the second fractionator 70, and the kerosene fraction is obtained from the middle section. On the other hand, hydrocarbons with a carbon number of $C_{10}$ or less are obtained from the top of the second fractionator 70 and supplied to the naphtha stabilizer 72.

Further, in the naphtha stabilizer 72, the hydrocarbons with a carbon number of $C_{10}$ or less which have been supplied from the naphtha fraction hydrotreating reactor 62 and the second fractionator 70 are distilled to separate and fractionate naphtha ($C_5$ to $C_{10}$) as final products. Thereby, high-purity naphtha is obtained from the bottom of the naphtha stabilizer 72. On the other hand, a flare gas including mainly hydrocarbons with a predetermined carbon number or less ($C_4$ or less), which is not a target product, is discharged from the top of the naphtha stabilizer 72. This flare gas is introduced into external combustion equipment (not shown in the drawing) and released into the atmosphere after combustion.

According to the hydrocarbon production apparatus of the present embodiment and the hydrocarbon production process by using the apparatus, the apparatus is provided with the light liquid hydrocarbon supply line 91 for supplying the light hydrocarbons having cloud points lower than a temperature at the outlet of the second cooler 86*a* in the second gas-liquid separating unit 86 on an upstream side line which is upstream from the second gas-liquid separating unit 86 (the last stage of the gas-liquid separating unit) in the gas-liquid separator 36. Therefore, for example, while a reaction is stopped in the reactor 30 or while a reaction conversion ratio is 20% or less in the reactor, the light hydrocarbons are supplied to the upstream side line. Thereby, it is possible to prevent the adhesion of wax to the second cooler 86*a* of the second gas-liquid separating unit 86 and also remove the adhered wax. Thus, it is possible to reliably prevent a trouble resulting from the adhesion of wax to a cooler of the gas-liquid separator 86 (for example, the second cooler 86*a*) during unsteady operation, without reduction in operation rate of the FT synthesis unit 5 or an increase in size and cost of facilities.

Further, one end of the light liquid hydrocarbon supply line 91 is connected to the second gas-liquid separator 86 (the last stage of the gas-liquid separating unit) of the gas-liquid separator 36 and connected to the second discharge line 86*d* (line) for discharging the liquid hydrocarbons from the above gas-liquid separator 86. Thus, the light liquid hydrocarbon supply line 91 can be made relatively short to suppress an increase in the size of the apparatus.

Still further, the other end of the light liquid hydrocarbon supply line 91 is connected to the connection line 87 positioned just before the second gas-liquid separating unit 86 (the last stage of the gas-liquid separating unit) of the gas-liquid separator 86. Thus, the light liquid hydrocarbon supply line 91 can be made relatively short to suppress an increase in the size of the apparatus.

Figure 3:
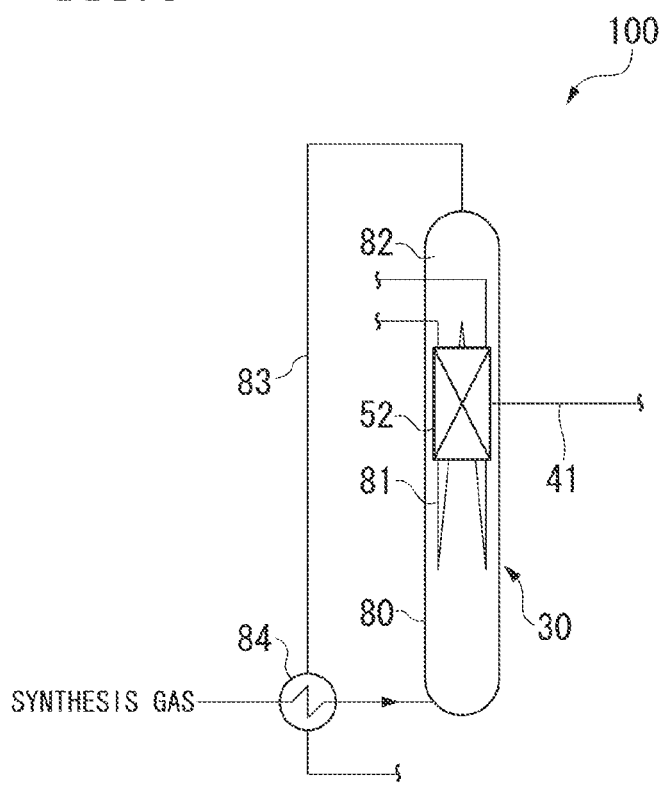
FIG. 3 is a schematic constitution diagram which shows a modified example of the FT synthesis unit of the present invention.

In the above-described embodiment, the FT synthesis unit 5 having the filter 52 for filtrating a slurry inside the separation vessel 50 of the external catalyst separator 34 is used to carry out the hydrocarbon production process of the present invention, to which the present invention shall not be limited. As shown in FIG. 3, the FT synthesis unit 100 having an internal-type catalyst separating mechanism in which the filter 52 is installed inside the reactor 30 may be used to produce hydrocarbons.

The FT synthesis unit 100 shown in FIG. 3 is different from the FT synthesis unit 5 shown in FIG. 2 in that the filter 52 is installed inside the reactor 30 in place of the external catalyst separator 34 to form the internal-type catalyst separating mechanism in the reactor 30. The catalyst separating mechanism is similar in constitution to that which is mainly composed of the filter 52 installed inside the separation vessel 50 of the external catalyst separator 34 shown in FIG. 2.

Further, the FT synthesis unit that carries out the hydrocarbon production process of the present invention includes a combination of an external-type catalyst separating mechanism with an internal-type catalyst separating mechanism. That is, the hydrocarbon production process of the present invention may be carried out by using an FT synthesis unit which is provided with the external catalyst separator 34 shown in FIG. 2 and the filter 52 inside the reactor 30 shown in FIG. 3.

Further, in the above-described embodiment, a natural gas is used as a hydrocarbon feedstock supplied to the liquid fuel synthesizing system 1. However, there may be used other hydrocarbon feedstock, for example, asphalt and residual oil.

Still further, in the above-described embodiment, the liquid fuel synthesizing system 1 is employed to describe a mode of carrying out the hydrocarbon production process of the present invention. The present invention is applicable to a hydrocarbon production process for synthesizing hydrocarbons by bringing a synthesis gas which contains at least hydrogen gas and carbon monoxide gas as main components into contact with a slurry including catalyst particles.

A detailed description has been so far given for the embodiments of the present invention with reference to the drawings. Specific constitutions shall not be limited to these embodiments but include any change in design within a scope not departing from the gist of the present invention.

EXAMPLE

The slurry bubble column reactor 30 shown in FIG. 2 was operated in such a manner that at the time of start up, a carbon monoxide conversion ratio was substantially reduced as compared with that during normal operation.

As a feedstock, the synthesis gas supplied from the synthesis gas production unit ($CO:H_2$ molar ratio=1:2) was supplied to the slurry bubble column reactor 30. In addition, operation was performed at reaction temperatures of 180° C. to 190° C. to set a reaction conversion ratio of carbon monoxide on passage of carbon monoxide through the reactor 30 at 5 to 10%.

At approximately 70 hours later from the start of the above operation, a naphtha fraction was started to be supplied from a tank (not shown in the drawing) installed in the line 75b for supplying the naphtha fraction to the naphtha fraction hydrotreating reactor 62 through a light liquid hydrocarbon supply line (not shown in the drawing) connected to the connection line 87 on the upstream side from the second cooler 86a of the second gas-liquid separating unit 86 of the gas-liquid separator 36 in FIG. 1. Examination of a cloud point (CP) of the supplied naphtha fraction has revealed that the naphtha fraction did not cloud at a temperature of −50° C., that is, the lowest temperature on determination. Therefore, the cloud point of the naphtha fraction is a temperature lower than the temperature of −50° C., and the naphtha fraction is a light hydrocarbon having the cloud point lower than a temperature at the outlet of the second cooler 86a during normal operation, that is approximately 35° C. to 40° C.

Figure 4:
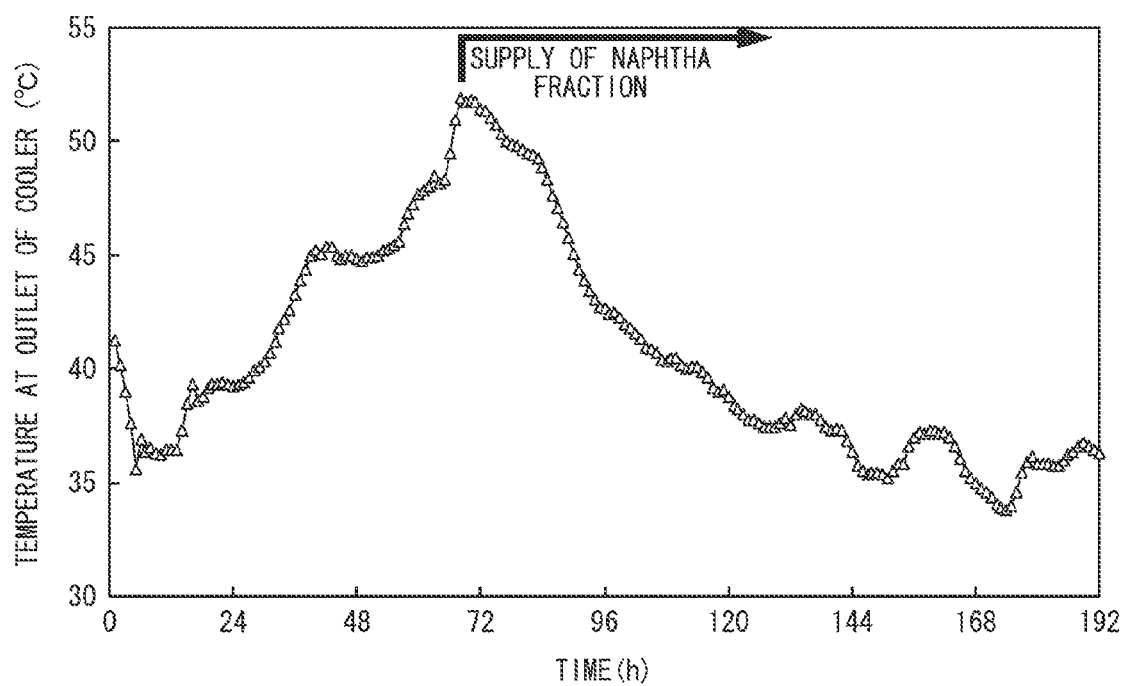
FIG. 4 is a graph which shows a change in temperature at an outlet of a second cooler over time.

FIG. 4 shows a change over time in temperature at the outlet of the second cooler 86a (cooler-outlet temperature) from the start of the above operation. The temperature at the outlet of the second cooler 86a rises over time from the start of the operation at a low reaction conversion ratio of carbon monoxide in the present example. This is considered due to the fact that a wax fraction contained in the liquid hydrocarbons constituting a slurry inside the reactor 30 is partially vaporized and cooled by the heat exchange unit 84 and the first cooler 85a after passing through the discharge line 83 connected to the top of the reactor 30, this wax fraction is further cooled by the second cooler 86a, by which at least a portion of the wax fraction is solidified and adhered thereon in the form of a solid or a semi-solid, resulting in reduced heat conduction and also in a failure of predetermined cooling.

That is, it is considered that since operation is performed at a low reaction conversion ratio of carbon monoxide, hydrocarbons to be produced are decreased in quantity, liquid components to be condensed inside the second cooler 86a are also decreased in quantity and, during normal operation, the wax fraction to be washed away by the liquid components is not removed but adhered and accumulated inside the second cooler 86a over time.

On the other hand, when a naphtha fraction was flowed through the connection line 87 on the upstream side from the second cooler 86a, the temperature at the outlet of the second cooler 86a was decreased over time. This is considered due to the fact that the wax fraction adhered and accumulated inside the second cooler 86a is partially dissolved again by the naphtha fraction and washed away to improve the heat conduction of the second cooler 86a, thus resulting in recovery of the cooling effect.

As described so far, it has been revealed that where operation is performed at a low reaction conversion ratio of carbon monoxide in the slurry bubble column reactor 30, predetermined liquid hydrocarbons are flowed on the upstream side of the second cooler 86a, thus making it possible to keep the cooling effect of the second cooler 86a equal to that during normal operation.

Where a nitrogen gas is substituted for a synthesis gas to recycle the nitrogen gas inside the reaction system, operation for supplying the naphtha fraction to the upstream side of the second cooler 86a also provides similar effects.

INDUSTRIAL APPLICABILITY

The present invention relates to a hydrocarbon production apparatus and a hydrocarbon production process by using a slurry bubble column reactor according to the Fischer-Tropsch synthesis reaction. The present invention is able to prevent occurrence of a trouble resulting from adhesion of wax to a cooler of a gas-liquid separating unit.

DESCRIPTION OF THE REFERENCE SIGNS

1: Liquid fuel synthesizing system
5: FT synthesis unit
30: Slurry bubble column reactor (reactor)
36: Gas-liquid separator
40: First fractionator
82: Gas phase portion
83: Discharge line
84: Heat exchange unit
85: First gas-liquid separating unit
86: Second gas-liquid separating unit
86a: Second cooler
87: Connection line
91: Light liquid hydrocarbon supply line

The invention claimed is:

1. A hydrocarbon production apparatus which retains internally slurry containing catalyst particles and liquid hydrocarbons to produce hydrocarbons by using a slurry bubble column reactor having a gas phase portion at an upper part of the slurry according to the Fischer-Tropsch synthesis reaction, the hydrocarbon production apparatus comprising:
a gas-liquid separator having a plurality of gas-liquid separating units for cooling hydrocarbons which have been drawn out from the gas phase portion of the reactor and are in a gaseous state under conditions inside the reactor, thereby liquefying a portion of the hydrocarbons to conduct gas-liquid separation, wherein each of the plurality of gas-liquid separating units is provided with:
a cooler;
a gas-liquid separation vessel;
a downstream side line which is downstream from the last stage of the gas-liquid separating unit of the gas-liquid separator, wherein a light liquid hydrocarbon line on the downstream side therein which light liquid hydrocarbons having cloud points lower than a temperature at an outlet of the cooler in the last stage of the gas-liquid separating unit are flowed therein;
an upstream side line which is upstream from the last stage of the gas-liquid separating unit of the gas-liquid separator; and
a light liquid hydrocarbon supply line which is disposed between the downstream side line and the upstream side line, and which supplies the light liquid hydrocarbons inside the light liquid hydrocarbon line on the downstream side to the upstream side line.

2. The hydrocarbon production apparatus according to claim 1, wherein the light liquid hydrocarbon line on the downstream side is a line which is connected to the last stage of the gas-liquid separating unit of the gas-liquid separator to discharge liquid hydrocarbons from the gas-liquid separating unit.

3. The hydrocarbon production apparatus according to claim 1, wherein
the upstream side line is a line positioned just before the last stage of the gas-liquid separating unit of the gas-liquid separator.

4. The hydrocarbon production apparatus according to claim 2, wherein
the upstream side line is a line positioned just before the last stage of the gas-liquid separating unit of the gas-liquid separator.

5. A hydrocarbon production process which retains internally slurry containing catalyst particles and liquid hydrocarbons to produce hydrocarbons by using a slurry bubble column reactor having a gas phase portion at an upper part of the slurry according to the Fischer-Tropsch synthesis reaction, the hydrocarbon production process comprising:
a gas-liquid separation step in which a gas-liquid separator having a gas-liquid separating unit composed of a cooler and a gas-liquid separation vessel is used to cool hydrocarbons which have been drawn out from the gas phase portion of the reactor and are in a gaseous state under conditions inside the reactor, thereby performing gas-liquid separation after liquefaction of a portion of the hydrocarbons, and
while a reaction is stopped in the reactor or while a reaction conversion ratio of carbon monoxide is 20% or less in the reactor, light liquid hydrocarbons having cloud points lower than a temperature at an outlet of the cooler in the last stage of the gas-liquid separating unit of the gas-liquid separator are supplied to an upstream side line which is upstream from the last stage of the gas-liquid separating unit of the gas-liquid separator.

6. The hydrocarbon production process according to claim 5, wherein as the light liquid hydrocarbons, there are used liquid hydrocarbons discharged from the last stage of the gas-liquid separating unit of the gas-liquid separator.

7. The hydrocarbon production process according to claim 6, wherein the light liquid hydrocarbons are supplied to a line positioned just before the last stage of the gas-liquid separating unit of the gas-liquid separator.

8. The hydrocarbon production process according to claim 5, wherein the light liquid hydrocarbons are supplied to a line positioned just before the last stage of the gas-liquid separating unit of the gas-liquid separator.

* * * * *